US011719679B2

(12) United States Patent
Johnson et al.

(10) Patent No.: US 11,719,679 B2
(45) Date of Patent: Aug. 8, 2023

(54) GAS EXCHANGE TRANSIENT BUFFERING SYSTEMS AND METHODS

(71) Applicant: Li-Cor, Inc., Lincoln, NE (US)

(72) Inventors: Mark A. Johnson, Lincoln, NE (US); Robert D. Eckles, Lincoln, NE (US); Douglas J. Lynch, Lincoln, NE (US); Johnathan I. E. McCoy, Lincoln, NE (US); Jason Hupp, Lincoln, NE (US)

(73) Assignee: LI-COR, INC., Lincoln, NE (US)

( * ) Notice: Subject to any disclaimer, the term of this patent is extended or adjusted under 35 U.S.C. 154(b) by 0 days.

(21) Appl. No.: 17/198,879

(22) Filed: Mar. 11, 2021

(65) Prior Publication Data

US 2021/0293768 A1 Sep. 23, 2021

Related U.S. Application Data

(60) Provisional application No. 62/992,618, filed on Mar. 20, 2020.

(51) Int. Cl.
 *G01N 33/00* (2006.01)
(52) U.S. Cl.
 CPC ................. *G01N 33/0098* (2013.01)
(58) Field of Classification Search
 CPC ........... G01N 33/0098; G01N 33/0004; G01N 33/0067
 See application file for complete search history.

(56) References Cited

U.S. PATENT DOCUMENTS

| 4,768,390 A | * | 9/1988 | Baker | ................... G01N 21/84 356/73 |
| 2006/0137041 A1 | * | 6/2006 | Masle | .................. C07K 14/415 800/287 |

(Continued)

FOREIGN PATENT DOCUMENTS

| CA | 3023404 A1 | * | 5/2019 | ............... A01G 7/02 |
| CN | 101380541 A | * | 3/2009 | |

(Continued)

OTHER PUBLICATIONS

JP-2013520318-A-translation (Year: 2013).*

(Continued)

*Primary Examiner* — Kristina M Deherrera
*Assistant Examiner* — Fatemeh Esfandiari Nia
(74) *Attorney, Agent, or Firm* — Gerald T. Gray; Leydig, Voit & Mayer, Ltd.

(57) ABSTRACT

Gas exchange analysis methods and systems utilize a water vapor buffering component including a material configured to buffer water vapor in a flow of a gas, whereby fluctuations in the water vapor content in the flow of the gas are slowed for components downstream from the water vapor buffering component. Components downstream of the water vapor buffering component may include: a first water vapor sensor configured to receive the flow of the gas from the water vapor buffering component and configured to measure a first concentration of water vapor in the gas; a sample chamber configured to receive the gas exiting the water vapor buffering component or the first water vapor sensor and to hold a sample capable of adding or removing water vapor from the gas; and a second water vapor sensor configured to measure a second concentration of water vapor in the gas exiting the sample chamber.

22 Claims, 4 Drawing Sheets

(56) References Cited

U.S. PATENT DOCUMENTS

| | | | |
|---|---|---|---|
| 2009/0178467 | A1 | 7/2009 | Liu et al. |
| 2010/0175699 | A1* | 7/2010 | Varney .............. A61M 16/0672 |
| | | | 128/204.23 |
| 2012/0073355 | A1 | 3/2012 | Johnson et al. |
| 2012/0074325 | A1* | 3/2012 | Johnson ................ G01N 21/05 |
| | | | 250/343 |
| 2015/0068277 | A1 | 3/2015 | Johnson et al. |
| 2016/0073930 | A1 | 3/2016 | Stetter et al. |
| 2016/0310622 | A1* | 10/2016 | Goetz ..................... A61L 2/206 |
| 2018/0313749 | A1* | 11/2018 | Enquist ............. G01N 33/0026 |
| 2019/0133052 | A1 | 5/2019 | Carson |
| 2020/0377927 | A1* | 12/2020 | Davis .................. C12Q 1/6806 |
| 2020/0408729 | A1 | 12/2020 | Welles et al. |

FOREIGN PATENT DOCUMENTS

| | | | |
|---|---|---|---|
| CN | 205333581 U | * | 6/2016 |
| JP | 2004073927 A | * | 3/2004 |
| JP | 2013520318 A | * | 1/2013 |

OTHER PUBLICATIONS

JP-2004073927-A-English (Year: 2004).*

Gillon et al., "Internal Conductance to CO2 Diffusion and C18OO Discrimination in C3 Leaves," American Society of Plant Biologists, Plant Physiology, vol. 123, May 2000.

Cosgrove-Davies et al., "A System for Measurement of Photosynthesis in the Aerial Portion of a Plant," Engineering 90 Senior Design Project, Environmental Science, May 8, 2008.

Barbour et al., "Variability in mesophyll conductance between barley genotypes, and effects on transpiration efficiency and carbon isotope discrimination," Blackwell Publishing Ltd, Plant, Cell & Environment 33, 1176-1185, 2010.

Whelan et al., "Carbonyl sulfide exchange in soils for better estimates of ecosystem carbon uptake, "Atmos. Chem. Phys., 16, 3711-3726, Mar. 21, 2016.

Evans et al., "Temperature response of carbon isotope discrimination and mesophyll conductance in tobacco," Blackwell Publishing Ltd, Plant, Cell and Environment 36, 745-756, 2013.

Barbour et al., "A new measurement technique reveals rapid post-illumination changes in the carbon isotope composition of leaf-respired CO2," Blackwell Publishing Ltd, Plant, Cell and Environment 30, 469-482, 2007.

Ren et al., "Carbon Dioxide Transport in Nation 1100 EW Membrane and in a Direct Methanol Fuel Cell," Journal of The Electrochemical Society, 162 (10) F1221-F1230, Aug. 10, 2015.

"Nation Ion Exchange Materials: Safety in Handling and Use," Technical Bulletin T-01, The Chemours Company FC, LLC, Fayetteville, NC, 2016.

Written Opinion of the International Searching Authority from the International Searching Authority for PCT/US2021/022127, dated Jun. 29, 2021.

International Search Report from the International Searching Authority for PCT/US2021/022127, dated Jun. 29, 2021.

Kölling et al., "A whole-plant chamber system for parallel gas exchange measurements of *Arabidopsis* and other herbaceous species," Plant methods, 2015, vol. 11, article No. 48, pp. 1-12.

Written Opinion of the International Searching Authority in International Application PCT/US2021/022127.

Kolling, K et al., A whole-plant chamber system for parallel gas exchange measurements of *Arabidopsis* and other herbaceous species, Plant Methods, 2015, vol. 11, article No. 48, internal pp. 1-12.

International Preliminary Report on Patentability in International Application PCT/US2021/022127.

\* cited by examiner

GAS EXCHANGE TRANSIENT BUFFERING SYSTEMS AND METHODS

CROSS-REFERENCE TO RELATED APPLICATION

This application claims the benefit of priority to U.S. Provisional Patent Application No. 62/992,618, filed Mar. 20, 2020, which is hereby incorporated by reference in its entirety.

BACKGROUND

Gas exchange measurement systems, such as systems for measuring plant photosynthesis and transpiration rates, can be categorized as open or closed systems. For open systems, a leaf or plant sample may be enclosed in a sample chamber, and an air stream is passed continuously through the chamber. $CO_2$ and $H_2O$ concentrations of chamber influent and effluent are measured, and the difference between influent and effluent concentration is calculated. (Throughout this document the term "concentration" refers to mole fraction of a gas in natural or synthetic moist air, or mole fraction in natural or synthetic dry air ("dry mole fraction") where such is specified.) This difference may be used, along with the mass flow rate, to calculate photosynthesis ($CO_2$) and transpiration ($H_2O$) rates. For closed systems, the leaf or plant is enclosed in a chamber that is not supplied with fresh air. The concentrations of $CO_2$ and $H_2O$ are continuously monitored within the chamber. The rate of change of this concentration, along with the chamber volume, may be used to calculate photosynthesis ($CO_2$) and transpiration ($H_2O$) rates.

Gas exchange systems are often used outdoors in plant canopies where the magnitude of ambient gas concentrations may be highly variable, and the rate of change may be significant. For example, water and carbon-dioxide concentrations in a canopy vary radically due to active plant transpiration and photosynthesis, and passive physical phenomena such as stratification and wind. Often, the conditions at which gas exchange measurements are taken outdoors are meant to mimic ambient conditions. These ambient conditions are most easily replicated in open gas exchange systems by using ambient air as the fresh air supply. A typical open gas exchange system can measure reasonable exchange rates in the presence of slow changes in ambient airstream water vapor or carbon dioxide concentrations. However, sufficiently fast transients can be misconstrued by the measurement system as gas exchange and introduce measurement errors.

In an example gas exchange system, an airstream passes over a sensor that measures incoming water vapor content (reference sensor), after which it passes through a cuvette containing biological material that adds or removes water vapor to the airstream, and finally passes over a second sensor (sample sensor) to measure outgoing water vapor content. Measurement errors in this system result if changes in the incoming water vapor content occur on a similar time-scale to that of the measurement. Sufficiently fast transients in water vapor concentrations reach the two sensors at different times, and a time lag between the reference and sample sensors results. Time lags result in the erroneously perceived introduction/removal of water vapor from the cuvette as calculated from the instantaneous difference between the reference and sample sensors. Moreover, transpirations rates become more difficult to interpret under transient ambient water vapor concentrations, and a nearly constant concentration during the measurement is most often desired.

Thus, there is a need for improved gas exchange analysis systems and methods for samples that may generate or remove water content from an airstream or gas flow.

SUMMARY

The present disclosure provides systems and method for reducing or minimizing the impact of ambient water vapor transients on measurements in a gas exchange measurement system. More generally, embodiments dampen or smoothout fast transients in ambient air supply, and allow for controlling the rate at which transients which are propagated through the measurement system, maintaining measurement performance while approximating ambient conditions, by buffering the in-coming air in the gas exchange measurement system. Advantageously, the incoming water vapor content is not controlled to a set humidity, but rather incoming rapid transients are smoothed such that i) rapid incoming transients do not create an erroneous measurement artifact, and ii) nearly constant conditions are maintained during a given measurement.

According to an embodiment, a gas exchange analysis system is provided that includes a water vapor buffering component, the water vapor buffering component including a material configured to buffer water vapor in a flow of a gas, whereby fluctuations in the water vapor content in the flow of the gas are slowed for components downstream from the water vapor buffering component in the gas exchange system, wherein the components downstream of the water vapor buffering component include: a first water vapor sensor configured to receive the flow of the gas from the water vapor buffering component and configured to measure a first concentration of water vapor in the gas; a sample chamber configured to receive the gas exiting the first water vapor sensor and to hold a sample capable of adding or removing water vapor from the gas; and a second water vapor sensor configured to measure a second concentration of water vapor in the gas exiting the sample chamber.

In another embodiment, a gas analysis system is provided that includes a first water vapor sensor configured to receive a flow of the gas from a first gas flow line and configured to measure a first concentration of water vapor in the gas received from the first gas flow line, a sample chamber configured to hold a sample capable of adding or removing water from the gas, a second water vapor sensor configured to measure a second concentration of water vapor in the gas exiting the sample chamber, and a water buffering component in the first gas flow line before the first water vapor sensor, the water buffering component including a material configured to buffer water vapor content in the flow of the gas, whereby fluctuations in water vapor content in the flow of the gas are slowed for components downstream from the water buffering component in the gas exchange system. The system may include a gas source configured to provide the flow of the gas.

In certain aspects, the material absorbs or desorbs water in the presence of a water concentration gradient. In certain aspects, the material includes a Nafion® structure. Nafion is a sulfonated tetrafluoroethylene based fluoropolymer-copolymer developed by DuPont. In certain aspects, the structure is selected from the group consisting of a bead, a tube and a flat membrane. In certain aspects, the material includes one or a plurality of Nafion beads. In certain aspects, the water buffering component includes a mechanism to adjust an amount of the material in the gas flow line, for example, the mechanism may be configured for dynamic adjustment of an amount of the material in the gas flow line.

In certain aspects, the gas exchange measurement system is a leaf porometer. In certain aspects, the sample includes a photosynthesis and/or transpiration capable material. In certain aspects, the first water vapor sensor includes one of a capacitive sensor, a resistive sensor, a thermal-conductivity-based sensor, or an optical absorption gas analyzer (e.g., NDIR or laser-based) or a laser-based gas analyzer and wherein the second water vapor sensor includes one of a capacitive sensor, a resistive sensor, a thermal-conductivity-based sensor, or an optical absorption gas analyzer or a second laser-based gas analyzer. The first and second water vapor sensors may be of the same type or of a different type.

According to another embodiment, a method of buffering water content in a gas exchange measurement system is provided. The method typically includes providing an incoming airstream to a first water vapor sensor, and buffering water vapor content in the incoming airstream using a water buffering component that absorbs or desorbs water in the presence of a water concentration gradient, whereby fluctuations in water vapor content in the incoming airstream are slowed for the first water vapor sensor and other components downstream from the water buffering component in the gas exchange measurement system.

In certain aspects, the first water vapor sensor is configured to measure a first concentration value of water vapor in the airstream entering a sample chamber, and the other components downstream of the water buffering component include at least the sample chamber, which is configured to hold a sample capable of adding or removing water from the airstream, and a second water vapor sensor configured to measure a second concentration value of water vapor in the airstream exiting the sample chamber.

In certain aspects, the first water vapor sensor is configured to measure a first concentration value of water vapor in the airstream exiting the water buffering component, and wherein the other components downstream of the water buffering component include at least: the sample chamber, configured to receive the airstream exiting the water buffering component and to hold a sample capable of adding or removing water from the airstream, and a second water vapor sensor configured to measure a second concentration value of water vapor in the airstream exiting the sample chamber.

In certain aspects, the method further includes continuously measuring the first water vapor concentration with the first water vapor sensor and continuously measuring the second water vapor concentration with the second water vapor sensor as the airstream continuously flows through or by the water buffering component, the first water vapor sensor, the sample chamber and the second water vapor sensor.

In certain aspects, the water buffering component includes a Nafion material. In certain aspects, the Nafion material has a structure selected from the group consisting of a bead, a tube and a flat membrane. In certain aspects, the water buffering component includes one or a plurality of Nafion beads.

In certain aspects, the method further includes adjusting an amount of surface area of the Nafion material exposed to the incoming airstream. For example, adjusting an amount of surface area may include removing beads or adding additional beads, changing a shape of a Nafion structure, adding or removing tubes, unrolling a rolled Nafion structure, etc.

According to an embodiment, a gas exchange analysis system is provided that includes an analyte buffering component, the analyte buffering component including a material configured to buffer a first analyte in a flow of a gas, whereby fluctuations in the first analyte content in the flow of the gas are reduced or slowed for components downstream from the analyte buffering component in the gas exchange system, wherein the components downstream of the analyte buffering component include: a analyte sensor configured to receive the flow of the gas from the analyte buffering component and configured to measure a first concentration of a target analyte in the gas, a sample chamber configured to hold a sample capable of adding or removing the analyte from the gas entering the sample chamber, and to 1) receive the gas exiting the first analyte sensor, or 2) receive the flow of the gas from the analyte buffering component, and a second analyte sensor configured to measure a second concentration of the target analyte in the gas exiting the sample chamber. In certain aspects, the analyte includes water and the material selectively absorbs or desorbs water in the presence of a water concentration gradient.

As used herein, adding water content or removing water content from an air stream may include outgassing, desorbing, a chemical reaction, a metabolic reaction, or other mechanisms for generating water content.

In certain aspects, a sample may include any material, substance or organism that exchanges, generates or consumes water. In certain aspects, the sample may include a water saturable or aqueous sample, which may include a photosynthesis capable material, substance or organism, such as a leaf or algae, or may include a respiratory material, substance or organism, e.g., a material that respires, or may include a metabolically active material, substance or organism.

In a further embodiment, a non-transitory computer readable medium is provided that stores instructions, which when executed by one or more processors, cause the one or more processors to implement a method of measuring a concentration of water vapor, and computing relevant variables such as transpiration and stomatal conductance, in a gas using a gas exchange measurement system as described herein.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE SEVERAL VIEWS OF THE DRAWINGS

The detailed description is described with reference to the accompanying figures. The use of the same reference numbers in different instances in the description and the figures may indicate similar or identical items.

DETAILED DESCRIPTION

The present disclosure provides systems and method for automatically reducing or minimizing the impact ambient water vapor transients may have on measurements in a gas exchange measurement system. In an example gas exchange system, an airstream passes over a sensor that measures incoming water vapor content (reference water vapor sensor), after which it passes through a sample chamber, e.g., cuvette, containing material that adds or removes water vapor to the airstream, and then passes over a second water vapor sensor (sample water vapor sensor) to measure outgoing water vapor content. Measurement errors in this system result if changes in the incoming water vapor content occur on the time-scale of the measurement. Sufficiently fast transients in water vapor concentrations reach the two sensors at different times, and a time lag between the reference and sample sensors results. Time lags result in the erroneously perceived introduction/removal of water vapor from the cuvette as calculated from the instantaneous difference between the reference and sample sensors. Moreover, transpiration rates become more difficult to interpret under transient ambient water vapor concentrations, and a constant concentration during the measurement is most often desired.

Embodiments advantageously alleviate this concern by slowing, in a controllable and/or user-selectable fashion, changes in water vapor concentration prior to the airstream reaching the incoming reference water vapor sensor. Certain embodiments use a specific material, Nafion, to buffer water vapor content in the air-stream of a gas exchange system. Nafion is a material that has a capacity to store water vapor. Nafion selectively exchanges water vapor in the presence of a concentration gradient following first order kinetics, and equilibrium is reached within milliseconds.

According to various embodiments, placing a certain quantity of Nafion in the flow-path, and ensuring proper interaction between the airstream and the Nafion, allows the water vapor in the airstream to be influenced by the water content held by the Nafion material, which is in turn influenced by previous water vapor concentration. The volume and surface area of the Nafion exposed to the airstream may be optimized to select the speed of transients which are propagated. Increasing water vapor concentration in the incoming air-stream will be absorbed by the Nafion, resulting in a slower rate of increase in the water concentration interacting with downstream components, e.g., sample chamber and water vapor sensors. Conversely, a decreasing water vapor concentration will desorb water from the Nafion, resulting in a slower rate of decrease in the water concentration interacting with downstream components. In this manner, the rate of water concentration changes in the in-coming airstream are slowed by the Nafion.

It will be appreciated that any other material that selectively buffers water vapor content may be used, for example, any water vapor selective element or membrane that allows water or water vapor to pass in a bi-directional manner dependent on the water concentration gradient at the surface of interaction.

It will also be appreciated that other analytes or gases of interest may be buffered using a material that selectively buffers the analyte or gas, e.g., a material which mimics the first-order kinetics of Nafion/water for that particular gas or analyte.

Figure 1A:
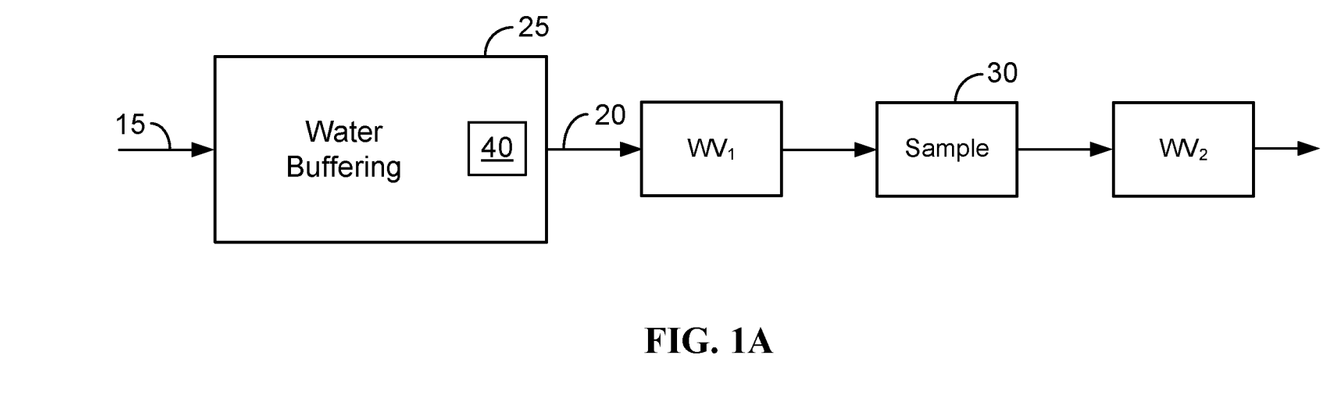
FIG. 1A illustrates a simplified flow and a physical arrangement of a gas exchange measurement system including a water vapor buffering component according to an embodiment.
Figure 1B:
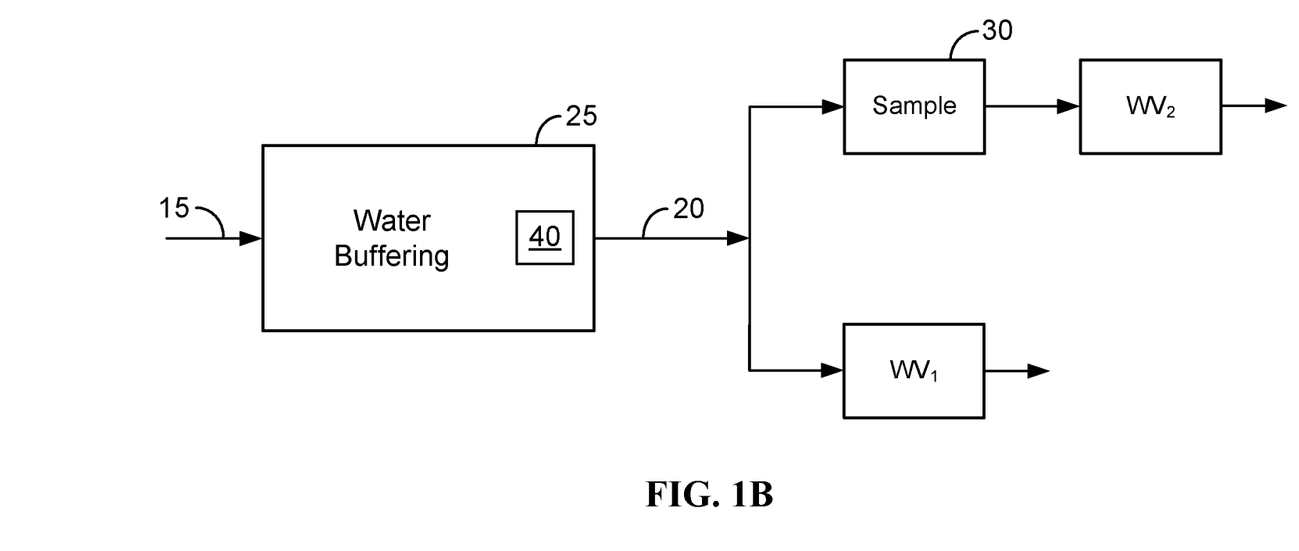
FIG. 1B illustrates a simplified flow and a physical arrangement of a gas exchange measurement system including a water vapor buffering component according to an embodiment.

FIG. 1A shows a simplified gas exchange measurement system 10 and gas flow diagram according to an embodiment. A water buffering component 25 receives an incoming flow (e.g., airstream) of gas from flow line 15 and provides a gas flow to downstream components via gas flow line 20. In the embodiment shown in FIG. 1A, the downstream components are arranged in series and include a first water vapor sensor ($WV_1$) that acts as a reference water vapor sensor, a sample chamber 30 and a second water vapor sensor ($WV_2$) that acts as a sample water vapor sensor. FIG. 1B shows a simplified gas exchange measurement system 10 and gas flow diagram according to another embodiment wherein the downstream components are arranged in parallel and include a first water vapor sensor ($WV_1$) that acts as a reference water vapor sensor, and a sample chamber 30 and a second water vapor sensor ($WV_2$) that acts as a sample water vapor sensor.

Water buffering component 25 includes a water vapor selective element 40 and effectively acts as a conditioned source of gas with any fluctuations in intensity of the water content in the incoming flow of gas smoothed out or slowed for the downstream components. For example, the water vapor selective element 40 may include a Nafion structure configured to interact with the airstream received from flow line 15. The Nafion structure may be configured as a one or a plurality of Nafion beads, or one or more Nafion sheets or as a tubular Nafion structure, or it may take on any other geometric configuration.

In operation, the first water vapor sensor ($WV_1$) receives the flow of the gas from the gas flow line 20 and measures the water concentration. The gas flow entering sample chamber then interacts with any sample material in the sample chamber. Such interaction may result in water vapor being added to, or removed from, the gas flow. The second water vapor sensor ($WV_2$) measures the water concentration of the gas flow exiting the sample chamber 30.

The first and second water vapor sensors may include a same type of humidity sensor or a different type of water vapor sensor. Examples of water vapor sensors include capacitive humidity sensors, resistive humidity sensors, thermal conductivity-based humidity sensors, hygrometers, optical humidity sensors, such as laser-based sensors, or other sensors as would be apparent to one skilled in the art.

In certain embodiments, the gas flow provided over gas flow line 15 may be received from the ambient surroundings, e.g., the gas flow includes a natural airstream from the vicinity of the system. In some embodiments, the gas flow may be provided from a controlled gas source. For example, in the context of photosynthesis and transpiration measurements, gas sources could include reservoirs of $CO_2$ and $H_2O$, and conditioning equipment for controlling and conditioning each gas concentration in a gas flow line.

In some embodiments, the water buffering component may be configured to controllably adjust the amount of Nafion interacting with the gas flow, e.g., in response to a control signal received from a control system. For example, the water buffering component may be configured to adjust a number of Nafion beads, or a surface area of a Nafion membrane, interacting with the gas flow, e.g., by inserting additional beads or additional membrane into the gas flow, or removing beads or membrane material from the gas flow.

Figure 2:
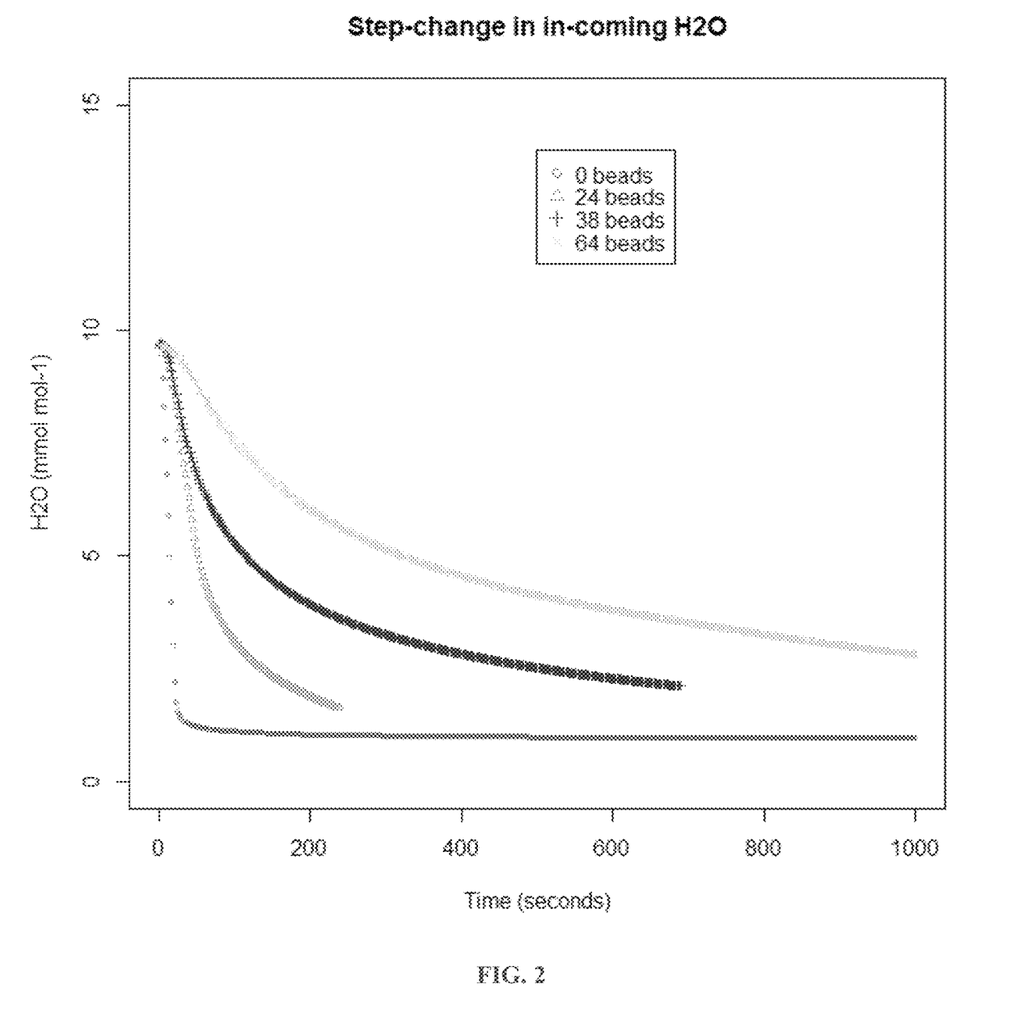
FIG. 2 shows that increasing the number of Nafion beads (e.g., 24 beads, 38 beads and 64 beads) further slows the rate-of-change of incoming water vapor content in the exiting air stream.
Figure 3:
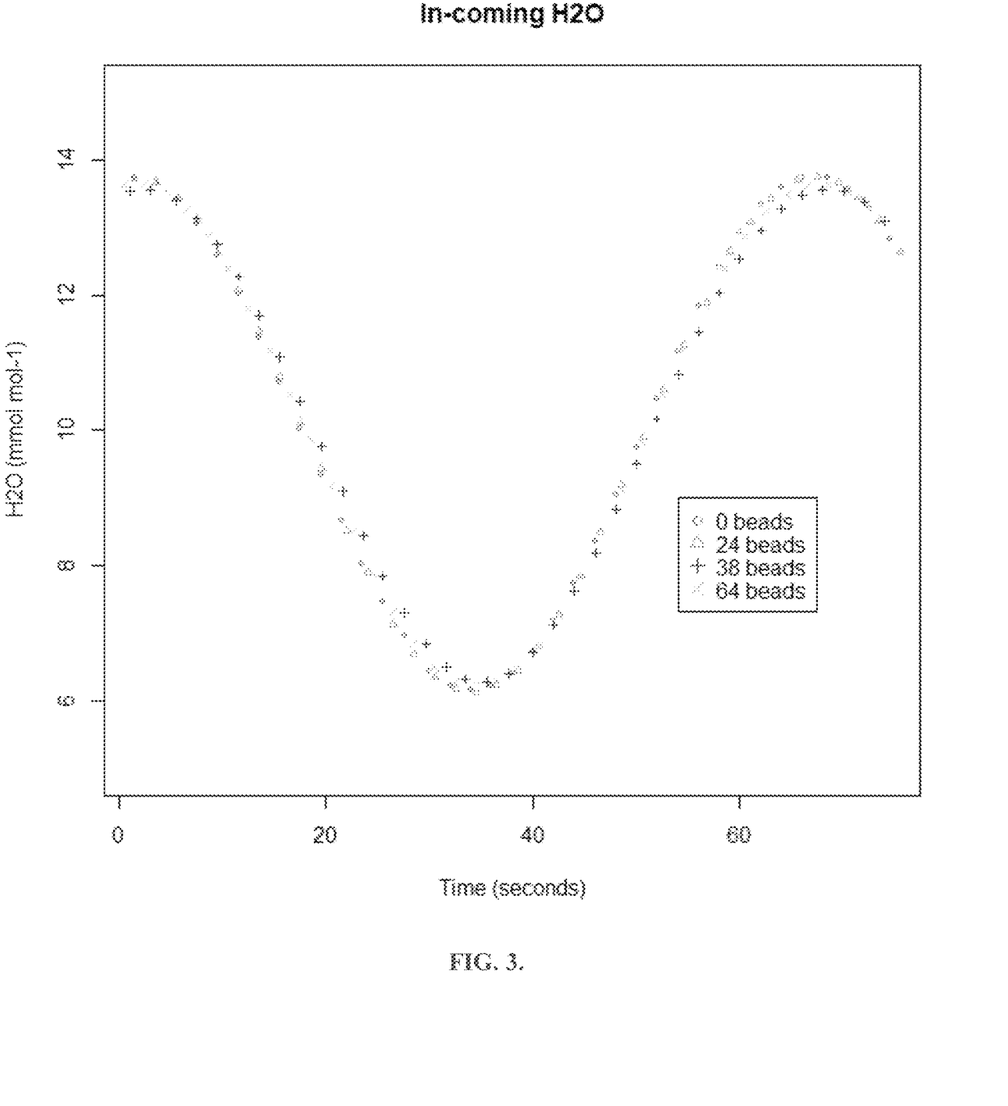
FIG. 3 illustrates incoming air water vapor concentrations as a function of time.
Figure 4:
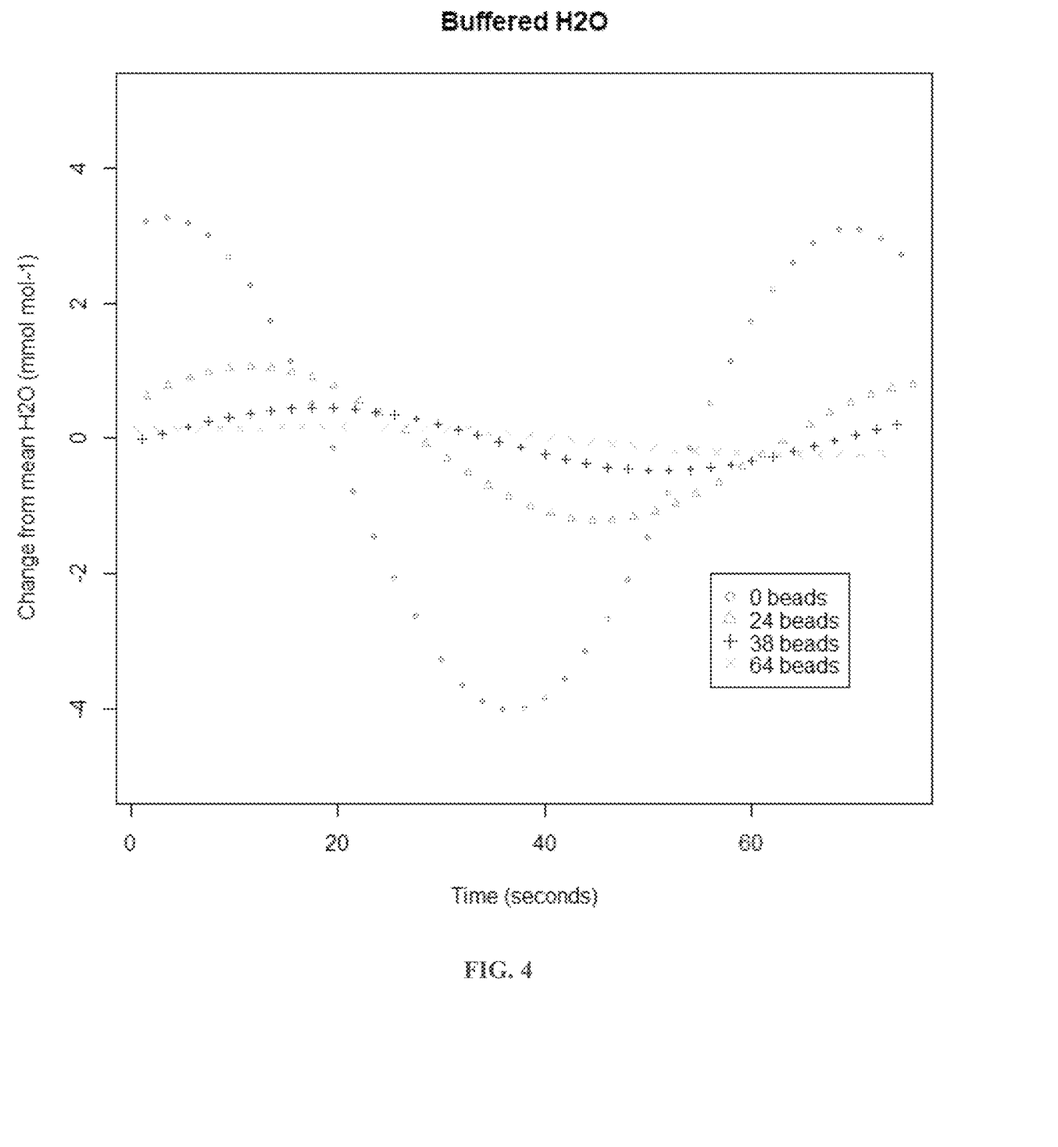
FIG. 4 illustrates the water vapor concentration exiting the water buffering element when subjected to the inlet variations (as shown in FIG. 3) for an increasing number of Nafion beads.

The effectiveness of using Nafion to buffer water vapor in an airstream has been demonstrated using an experimental arrangement including short lengths of tubing containing a number of spherical Nafion beads. The beads were installed in the flow-path between two non-dispersive infra-red (NDIR) gas analyzers. Changes to the in-coming water vapor content were dynamically controlled. FIGS. 2-4 demonstrate the effectiveness of Nafion in slowing the rate of incoming water vapor content.

The experimental arrangement consisted of a single conditioned air stream passing through a first water vapor analyzer, a water buffering element, and a second water vapor analyzer in series. The results in FIG. 2 illustrate the water concentration exiting the water buffering element, as measured by the second water vapor analyzer. The water vapor content of the conditioned air stream could be arbitrarily controlled. The function of the water vapor buffering element could be optimized by adjusting the number of Nafion beads (e.g., 3-4 mm in diameter) contained in the buffering element. The input water vapor concentration was decreased suddenly from approximately 10 mmol/mol to approximately 2 mmol/mol. The circular symbols (representing 0 beads) represents the water concentration exiting the water buffering element with no Nafion beads, and thus essentially follows the step change in the input concentration. FIG. 2 shows that increasing the number of Nafion beads (e.g., 24 beads, 38 beads and 64 beads) further slows the rate-of-change in the exiting air stream. Regardless of the number of beads added, the concentration eventually reaches in the input air stream concentration given sufficient time.

FIG. 3 illustrates incoming air water vapor concentrations as a function of time. The incoming air stream is not affected by the addition of Nafion beads, but there is some inherent minor variability in the method used to create the concentration variation.

FIG. 4 illustrates the water vapor concentration exiting the water buffering element when subjected to the inlet variations (as shown in FIG. 3) for an increasing number of Nafion beads. The values are presented as the variation above/below the mean water concentration. For 0 beads, the exit air water concentration effectively follows the input values. As the number of beads in the water buffering element is increased, the water vapor rate-of-change is progressively slowed. Because the input water concentration is sinusoidally varying, slowing of the rate-of-change (which can be adjusted based on the number of beads) prevents the exit air stream from rising as high as, or falling as low as, the input stream.

The various embodiments herein are particularly useful for conducting stomatal conductance measurements. For example, the embodiments are useful for buffering an incoming and otherwise natural ambient airstream that has very rapid water vapor transients. The Nafion "buffer" is able to slow rapid transient fluctuations in real time so that a stomatal conductance measurement does not have artifacts/errors related to (what would otherwise be) rather large fluctuating water vapor transients entering the sample (leaf) chamber during the measurement. The duration of the measurement, along with the maximum rate-of-change in ambient humidity, are used to optimize the performance of the buffering function. The reference (incoming air) humidity measurement is also more stable, allowing the stomatal conductance measurement to be specified at a nominal humidity.

In certain embodiments, a control system (not shown), e.g., including one or more processors and associated memory, may be provided to control various system components, e.g., to control the flow of gas in system 10. For example, the control system may control the flow rate or the amount or concentration of a gas and/or an analyte (e.g., water vapor concentration) in the gas provided. In an embodiment, the control system initiates real-time water vapor concentration measurements.

In certain embodiments, the control system or other intelligence module, which may include a processing component or components such as one or more processors and associated memory and/or storage, is configured to control, and to receive and process data from, the measurement devices to implement the methods disclosed herein, e.g., real-time concentration measurements of water vapor concentration and/or other analyte concentration or properties of interest.

Each processor or processing component is configured to implement functionality and/or process instructions for execution, for example, instructions stored in memory or instructions stored on storage devices, and may be implemented as an ASIC including an integrated instruction set. A memory, which may be a non-transient computer-readable storage medium, is configured to store information during operation. In some embodiments, a memory includes a temporary memory or area for information not to be maintained when the processing component is turned OFF. Examples of such temporary memory include volatile memories such as random access memories (RAM), dynamic random access memories (DRAM), and static random access memories (SRAM). The memory maintains program instructions for execution by the processing component.

Storage devices also include one or more non-transient computer-readable storage media. Storage devices are generally configured to store larger amounts of information than the memory. Storage devices may further be configured for long-term storage of information. In some examples, storage devices include non-volatile storage elements. Non-limiting examples of non-volatile storage elements include magnetic hard disks, optical discs, floppy discs, flash memories, or forms of electrically programmable memories (EPROM) or electrically erasable and programmable (EEPROM) memories.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the disclosed subject matter (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or example language (e.g., "such as") provided herein, is intended merely to better illuminate the disclosed subject matter and does not pose a limitation on the scope of the invention unless otherwise claimed. No language in the specification should be construed as indicating any non-claimed element as essential to the practice of the invention.

Certain embodiments are described herein. Variations of those embodiments may become apparent to those of ordinary skill in the art upon reading the foregoing description. The inventors expect skilled artisans to employ such variations as appropriate, and the inventors intend for the embodiments to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A gas exchange analysis system, the system comprising:
    a first water vapor sensor configured to receive a flow of a gas from a first gas flow line and configured to measure a first concentration of water vapor in the gas received from the first gas flow line;
    a sample chamber configured to hold a sample capable of adding or removing water from the gas and configured to receive the gas exiting the first water vapor sensor or receive the flow of the gas from the first gas flow line;
    a second water vapor sensor configured to measure a second concentration of water vapor in the gas exiting the sample chamber; and
    a component in the first gas flow line before the first water vapor sensor and before the sample chamber, the component including an amount of a material, wherein the material absorbs water in the presence of a positive water concentration gradient and desorbs water in the presence of a negative water concentration gradient to thereby control a rate of fluctuations in water vapor content propagated in the flow of the gas to the first water vapor sensor and to the sample chamber from the component in the gas exchange system.

2. The system of claim 1, wherein the material includes a Nafion structure.

3. The system of claim 2, wherein the structure is selected from the group consisting of a bead, a tube and a flat membrane.

4. The system of claim 1, wherein the material includes one or a plurality of Nafion beads.

5. The system of claim 1, wherein the gas exchange analysis system is a leaf porometer.

6. The system of claim 1, wherein the sample includes a photosynthesis and/or transpiration capable material.

7. The system of claim 1, wherein the first water vapor sensor includes one of a capacitive sensor, a resistive sensor, a thermal-conductivity-based sensor, an optical absorption gas analyzer, or a laser-based gas analyzer and wherein the second water vapor sensor includes one of a capacitive sensor, a resistive sensor, a thermal-conductivity-based sensor, an optical absorption gas analyzer, or a laser-based gas analyzer.

8. A method of reducing fluctuations of water content provided to a sample chamber in a gas exchange measurement system, the method comprising:
    providing an incoming airstream having a variable water vapor content;
    reducing water vapor content fluctuations in the incoming airstream using a component including a material that absorbs or desorbs water in the presence of a water concentration gradient, wherein the material absorbs water in the presence of a positive water concentration gradient and desorbs water in the presence of a negative water concentration gradient to thereby control a rate of fluctuations in the variable water vapor content in the incoming airstream propagated to a sample chamber downstream from the component in the gas exchange measurement system, wherein the sample chamber is configured to hold a sample capable of adding or removing water from the airstream.

9. The method of claim 8, wherein the component includes a Nafion material.

10. The method of claim 9, wherein the Nafion material has a structure selected from the group consisting of a bead, a tube and a membrane.

11. The method of claim 9, further including adjusting an amount of surface area of the Nafion material exposed to the incoming airstream.

12. The method of claim 8, wherein the component includes one or a plurality of Nafion beads.

13. The method of claim 8, wherein the gas exchange system includes a first water vapor sensor configured to measure a first concentration value of water vapor in the airstream entering the sample chamber, and
    a second water vapor sensor configured to measure a second concentration value of water vapor in the airstream exiting the sample chamber.

14. The method of claim 13, wherein the first water vapor sensor includes one of a capacitive sensor, a resistive sensor, a thermal-conductivity-based sensor, an optical absorption gas analyzer, or a laser-based gas analyzer and wherein the second water vapor sensor includes one of a capacitive sensor, a resistive sensor, a thermal-conductivity-based sensor, an optical absorption gas analyzer, or a laser-based gas analyzer.

15. The method of claim 13, further comprising continuously measuring the first water vapor concentration with the first water vapor sensor and continuously measuring the second water vapor concentration with the second water vapor sensor as the airstream continuously flows through or by the component, the first water vapor sensor, the sample chamber and the second water vapor sensor.

16. The method of claim 13, wherein the first water vapor sensor is arranged in parallel with the sample chamber.

17. The method of claim 8, wherein the first water vapor sensor is configured to measure a first concentration value of water vapor in the airstream exiting the component, and wherein the other components downstream of the component include at least:
    the sample chamber, configured to receive the airstream exiting the component and to hold a sample capable of adding or removing water from the airstream, and a second water vapor sensor configured to measure a second concentration value of water vapor in the airstream exiting the sample chamber.

18. The system of claim 8, wherein the first water vapor sensor receives the flow of gas from the component in parallel with the sample chamber receiving gas from the component.

19. A gas exchange analysis system, the system comprising:
   a component including an amount of a material that absorbs or desorbs water in the presence of a water concentration gradient, wherein the material absorbs water in the presence of a positive water concentration gradient and desorbs water in the presence of a negative water concentration gradient to thereby control a rate of fluctuations in the water vapor content in the flow of the gas propagated to components downstream from the component in the gas exchange system, wherein the components downstream of the component include:
   a first water vapor sensor configured to receive the flow of the gas from the component and configured to measure a first concentration of water vapor in the gas;
   a sample chamber configured to hold a sample capable of adding or removing water vapor from the gas entering the sample chamber, and configured to 1) receive the gas exiting the first water vapor sensor, or 2) receive the flow of the gas from the component; and
   a second water vapor sensor configured to measure a second concentration of water vapor in the gas exiting the sample chamber.

20. The system of claim 19, wherein the material includes a Nafion structure.

21. The system of claim 20, wherein the structure is selected from the group consisting of a bead, a tube and a membrane.

22. The system of claim 19, wherein the material includes one or a plurality of Nafion beads.

* * * * *